US006876722B2

United States Patent
Suzuki et al.

(10) Patent No.: US 6,876,722 B2
(45) Date of Patent: Apr. 5, 2005

(54) X-RAY INSPECTION SYSTEM

(75) Inventors: Makoto Suzuki, Hamamatsu (JP); Hiroshige Mori, Hamamatsu (JP); Tomikazu Yonezawa, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 304 days.

(21) Appl. No.: 10/257,004

(22) PCT Filed: Apr. 6, 2001

(86) PCT No.: PCT/JP01/02989
§ 371 (c)(1),
(2), (4) Date: Oct. 7, 2002

(87) PCT Pub. No.: WO01/77653
PCT Pub. Date: Oct. 18, 2001

(65) Prior Publication Data
US 2003/0142784 A1 Jul. 31, 2003

(30) Foreign Application Priority Data
Apr. 6, 2000 (JP) ........................... 2000-105225

(51) Int. Cl.⁷ ............................................. G01N 23/04
(52) U.S. Cl. .................. 378/57; 378/98.2; 250/214 VT
(58) Field of Search .......................... 378/57, 98, 98.2, 378/98.3; 250/214 VT; 313/523–529, 542–544, 537

(56) References Cited

U.S. PATENT DOCUMENTS 4,578,802 A * 3/1986 Itoh ............................ 378/41
5,194,726 A * 3/1993 Jonkman ............... 250/214 VT
5,367,552 A * 11/1994 Peschmann .................. 378/57
6,628,745 B1 * 9/2003 Annis et al. .................. 378/21

FOREIGN PATENT DOCUMENTS

| JP | S49-10085 | 1/1974 |
| JP | S53-48045 | 12/1978 |
| JP | S63-100360 | 5/1988 |
| JP | H6-311981 | 11/1994 |
| JP | H10-206352 | 8/1998 |
| JP | H11-108858 | 4/1999 |

* cited by examiner

Primary Examiner—Craig E. Church
Assistant Examiner—Thomas R Artman
(74) Attorney, Agent, or Firm—Morgan, Lewis & Bockius LLP

(57) ABSTRACT

The X-ray inspection system 10 comprises an X-ray electron conversion face 42 for converting an entered X-ray image transmitted through the measurement object into an electronic image, an output fluorescent face 46 for emitting fluorescence when an electronic image is entered, and deflecting means 44 which is installed between the X-ray electron conversion face 42 and output fluorescent face 46, wherein the electronic image which was entered and converted at the X-ray electron conversion face 42 is converged into a predetermined area on the output fluorescent face 46 by the deflecting means 44 so as to make the X-ray fluoroscopic image of the moving measurement object stand still on the output fluorescent face 46. By this, the image of the measurement object can be captured during the time when the X-ray fluorescence image is standing still, so sensitivity can be secured while increasing the resolution.

8 Claims, 17 Drawing Sheets

X-RAY INSPECTION SYSTEM

TECHNICAL FIELD

The present invention relates to an x-ray inspection system for inspecting a measurement object based on the X-ray fluoroscopic image of the measurement object which is moving at a predetermined speed, and more particularly to an in-line non-destructive inspection system for inspecting a measurement object which is being carried by a belt conveyor.

BACKGROUND ART

X-ray inspection systems using X-rays have been known as systems for inspecting the internal state of a measurement object non-destructively. The X-ray inspection system irradiates an X-ray, which is output being diverged from one point of the X-ray source in a predetermined angle direction, onto the measurement object, and capturing the image of the X-ray which transmitted through the measurement object using an X-ray image capturing unit, so as to inspect the internal status of the measurement object.

Japanese Patent Laid-Open No. 11-108858 discloses an X-ray inspection system which inspects a plurality of measurement objects which move on a line, such as a belt conveyor, one after another, using the above mentioned X-ray inspection system. An object of this X-ray inspection system is to obtain a clear X-ray fluoroscopic image while capturing the X-ray image of the moving measurement object. In other words, when the measurement object passes on a line between the X-ray source and X-ray image capturing unit, a gate signal is sent to the X-ray image capturing unit, operation of the X-ray image capturing unit is controlled by this gate signal, and an X-ray fluoroscopic image is captured at the moment when the measurement object crosses between the X-ray source and X-ray image capturing unit.

DISCLOSURE OF THE INVENTION

The above mentioned X-ray inspection system, however, has a problem in terms of sensitivity. In other words, as the moving speed of the measurement object increases, the image capturing time by the X-ray image capturing unit must be decreased to obtain the required resolution, but if the image capturing time decreases, the quantity of transmitted X-rays received by the X-ray image capturing unit inevitably decreases, and sensitivity drops.

With the foregoing in view, it is an object of the present invention to solve the above problem and to provide an X-ray inspection system which can implement both the required resolution and sufficient sensitivity in the X-ray image capturing of the moving measurement object.

An X-ray inspection system according to the present invention comprises an X-ray source for irradiating an X-ray onto a moving measurement object, an X-ray image capturing unit which has an X-ray electron conversion face for converting the entered X-ray image corresponding to the measurement object into an electronic image, and an output face where the electronic image emitted from the X-ray electron conversion face enters and the X-ray fluoroscopic image of the measurement object corresponding to the entered electronic image is output, position detecting means for detecting the position of the measurement object, and deflecting means for deflecting the flow of the electronic image from the X-ray electron conversion face to the output face, forming an electronic image on a predetermined area on the output face based on the position of the measurement object detected by the position detecting means.

By providing a deflecting means between the X-ray electron conversion face and the output face in this way, the progressing direction of the electronic image, which is converted by the X-ray electron conversion face and is emitted, can be deflected based on the position of the measurement object. As a result, even when the X-ray which transmitted through the moving measurement object enters a different position of the X-ray electron conversion face, an X-ray fluoroscopic image can be formed on a predetermined area of the output face.

The above mentioned X-ray inspection system may be characterized in that the X-ray source is a pulse X-ray source which outputs an X-ray when the measurement object is within the image capturing range of the X-ray image capturing unit. By using a pulse X-ray source in this way, the X-ray dose onto the moving measurement object can be decreased. If an X-ray is output only when the measurement object is within the image capturing range, the output of X-rays, which has the risk of having a negative influence on the human body, can be controlled.

The above mentioned X-ray inspection system may be characterized in that the X-ray image capturing unit further comprises an electrode which controls the flow of electronic images to the output face by applying a voltage between the X-ray electron conversion face and output face. By comprising an electrode which controls the flow of electronic images to the output face in this way, the image capturing time for the measurement object by the X-ray image capturing unit can be controlled. By this, the resolution of the X-ray fluoroscopic image of the moving measurement object can be improved.

The above mentioned X-ray inspection system may be characterized in that the X-ray image capturing unit further comprises an electrode which controls the flow of electronic images to the output face by applying voltage between the X-ray electron conversion face and output face, the electrode cancels the control of the flow of electronic images after an X-ray is output from the pulse X-ray source, and controls the flow of electronic images before the output of an X-ray from the pulse the pulse X-ray source is stopped. By controlling the flow of electronic images by the voltage to be applied between the X-ray electron conversion face and output face using the electrode, it can be controlled such that the X-ray image capturing unit does not capture an image in an unstable section which is generated at the rise or fall of the pulse X-ray, so that images can be captured by an X-ray with stable intensity.

The above mentioned X-ray inspection system may be characterized in that the X-ray source is a point light source, and the output face is a fluorescent face which emits fluorescence by the entry of electronic images.

The above mentioned X-ray inspection system may be characterized in that the position detecting means further comprises measurement object detecting means for detecting the measurement object before reaching the image capturing range of the X-ray image capturing unit, and the position of the measurement object in the image capturing range is determined based on the detection of the measurement object by the measurement object detecting means and the elapsed time from the time when the measurement object is detected. By detecting the measurement object which is moving in a predetermined direction at a predetermined speed using the measurement object detecting means before the measurement object reaches the image capturing range of the X-ray, the position of the measurement object in the X-ray image capturing range can be easily calculated from the detection time and elapsed time.

The above mentioned X-ray inspection system may be characterized in that the measurement object detecting means further comprises one light emitting element which emits light onto the measurement object and two light receiving elements which are installed at different locations and which receive light output from the light emitting element, and the distance between the moving path of the measurement object and the light emitting element is detected from the time interval of the time when the light output from the light emitting element to each light receiving element is blocked by the measurement object. By receiving light output from one light emitting element at the two light receiving elements installed at different locations and by detecting the time when the measurement object is detected by each light receiving element as described above, the distance between the moving path of the measurement object which is moving in a predetermined direction at a predetermined speed and the light emitting element can be easily calculated.

The above mentioned X-ray inspection system is an X-ray inspection system comprising an X-ray source and X-ray image capturing unit which are installed facing each other, sandwiching the measurement object passing path, wherein the X-ray image capturing unit further comprises an X-ray electron conversion material, and an output fluorescent face which is installed facing the X-ray electron conversion material, and the X-ray image capturing unit deflects the flow of electronic images between the X-ray electron conversion material and the output fluorescent face at a speed synchronizing with the moving speed of the measurement object.

Since the flow of electronic images between the X-ray electron conversion material and the output fluorescent face is deflected at a speed synchronizing with the moving speed of the measurement object, the image capturing time of the measurement object P can be increased, therefore both the required resolution and sufficient sensitivity can be implemented. Also it is preferable that the above mentioned X-ray inspection system starts deflection according to a predetermined trigger, which is generated based on the position of the measurement object.

BEST MODES FOR CARRYING OUT THE INVENTION

Embodiments of the X-ray inspection system according to the present invention will now be described in detail with reference to the accompanying drawings. In the description of the drawings, the same elements are denoted by the same symbol, where redundant descriptions are omitted.

Figure 1:
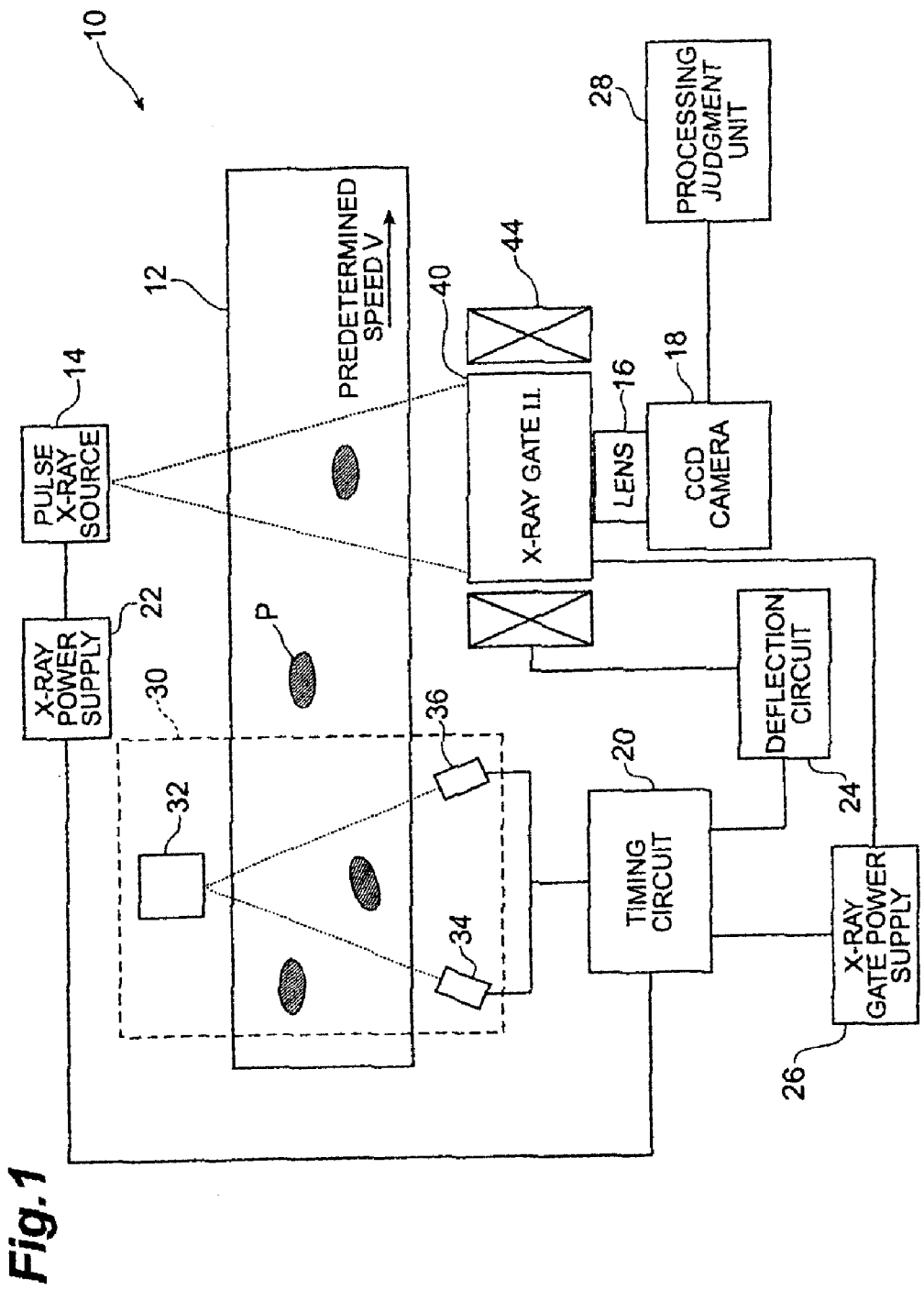
FIG. 1 is a block diagram depicting an X-ray inspection system according to the first embodiment.

FIG. 1 is a block diagram depicting the X-ray inspection system 10 of the present embodiment. The X-ray inspection system 10 is used for inspecting the tablets (measurement objects) P which are placed on a belt conveyor 12 and which are moving in a predetermined direction. The X-ray inspection system 10 is comprised of a belt conveyor 12 for transporting the placed tablets P at a predetermined speed V, a pulse X-ray source 14 for irradiating the pulse X-rays onto the tablets P on the belt conveyor 12, an X-ray gate image intensifier (hereafter "X-ray gate I•I") 40 which faces the pulse X-ray source 14, sandwiching the belt conveyor 12, a CCD camera 18 for capturing X-ray fluorescent images obtained by the X-ray gate I•I 40, and a processing judgment device 28 for judging the acceptance of the tablets P based on the captured X-ray fluorescent images and performing such processing as sorting. Between the X-ray gate I•I 40 and the CCD camera 18, a lens 16 for forming the X-ray fluorescent images obtained by the X-ray gate I•I 40 at the light receiving section of the CCD camera 18 is installed.

The measurement object detecting means 30 is installed at the upstream of the belt conveyor 12 in the image capturing range where the X-ray image is captured. The measurement object detecting means 30 is comprised of a light emitting diode 32 which emits light onto the tablets P on the belt conveyor 12, and two photo-diodes 34 and 36 which are disposed in parallel with the belt conveyor 12, sandwiching the belt conveyor 12. The two photo-diodes 34 and 36 are connected to the timing circuit 20. By these, the timing circuit 20 can calculate the position of the tablet P moving at a predetermined speed V based on the time when the photo-diodes 34 and 36 detected the tablet P and the elapsed time from the detection time.

The timing circuit 20 is connected to the X-ray power supply 22 for controlling an X-ray which is output from the pulse X-ray source 14, X-ray gate power supply 26 which opens/closes the gate of the X-ray gate I•I 40, and deflection circuit 24 for controlling the deflection coil 44 which is installed surrounding the X-ray gate I•I 40, and controls the respective operation timing by the timing signals.

Since the time when the tablet P arrives in a space between the X-ray source 14 and the X-ray gate I•I 40 can be determined, deflection can be started synchronizing with the arrival time, and the flow of electronic images can be deflected synchronizing with the moving speed of the tablet P. In other words, the output of the timing circuit 20 is a predetermined trigger which is generated based on the position of the tablet P, and the above mentioned deflection is started according to this trigger.

Figure 2:
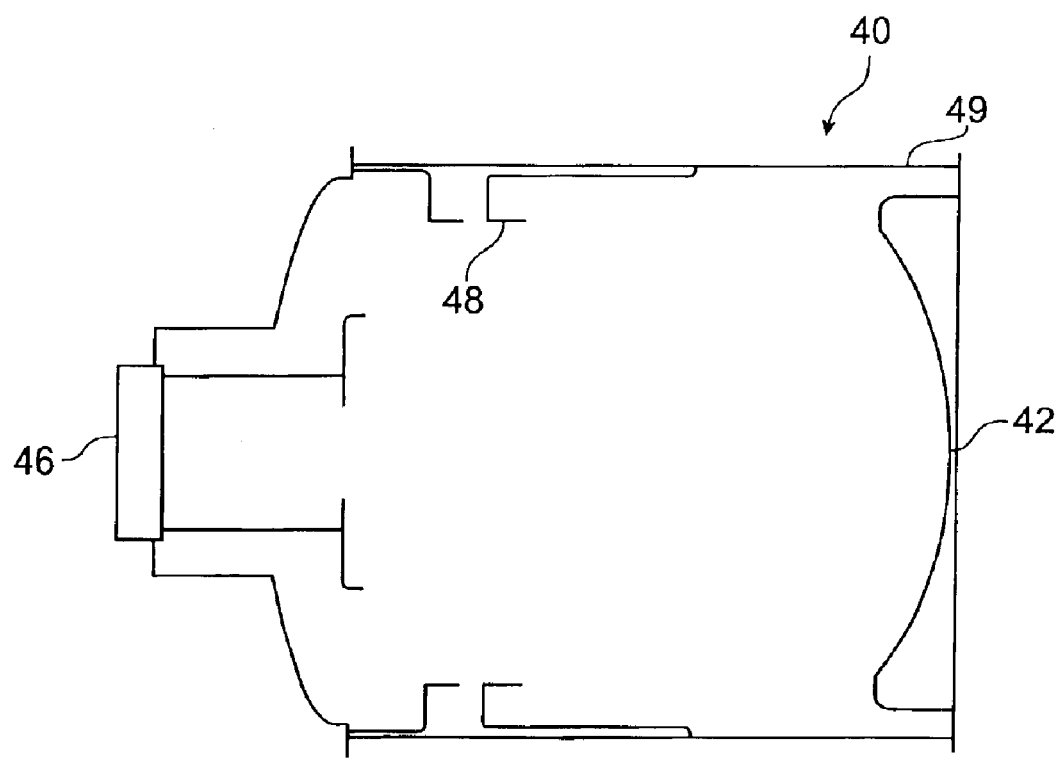
FIG. 2 is a cross-sectional view depicting the X-ray gate I•I.

Now the X-ray gate I•I 40 will be described. FIG. 2 is a cross-sectional view depicting the X-ray gate I•I 40. The X-ray gate I•I 40 is comprised of the X-ray electron conversion face 42 which converts the entered X-ray images into electronic images, and the output fluorescent face 46 which emits fluorescence when an electronic image enters, which are sealed in a container 49 in which pressure is reduced almost to a vacuum. An accelerating electrode 48 is installed around the inner wall of the container 49, and by controlling the voltage to be applied to the accelerating electrode 48, the gate of the X-ray gate I•I 40 can be controlled. In other words, if the output fluorescent face 46 side has high potential, the electronic images flowing from the X-ray electron conversion face 42 to the output fluorescent face 46 are accelerated, and if, on the other hand, the output fluorescent face 46 side has low potential, the flow of the electronic images from the X-ray electron conversion face 42 to the output fluorescent face 46 is controlled.

Next operation of the X-ray inspection system 10 will be described. The tablets P, which are the measurement objects, are placed on the belt conveyor 12 and are moving to the right in FIG. 1 at a predetermined speed V. When the tablet P blocks light which is output from the light emitting diode 32 to the first photo-diode 34, the time (hereafter "first light blocking time") is transmitted from the first photo-diode 34 to the timing circuit 20. When the tablet P is transported by the belt conveyor 12 and blocks the light which is output from the light emitting diode 32 to the second photo-diode 36, the time (hereafter "second light blocking time") is transmitted from the second photo-diode 36 to the timing circuit 20.

The timing circuit 20 detects the position of the table P based on the second light blocking time transmitted from the second photo-diode 36. In other words, the transporting speed V of the belt conveyor 12 is predetermined, so the timing circuit 20 can calculate the current position of the tablet P based on the second light blocking time and the elapsed time from the second light blocking time. And based on this positional information, that is, the elapsed time from the second light blocking time, the timing circuit 20 outputs the timing signal to the pulse X-ray power supply 22, deflection circuit 24, and X-ray gate power supply 26, for control.

Figure 3A:
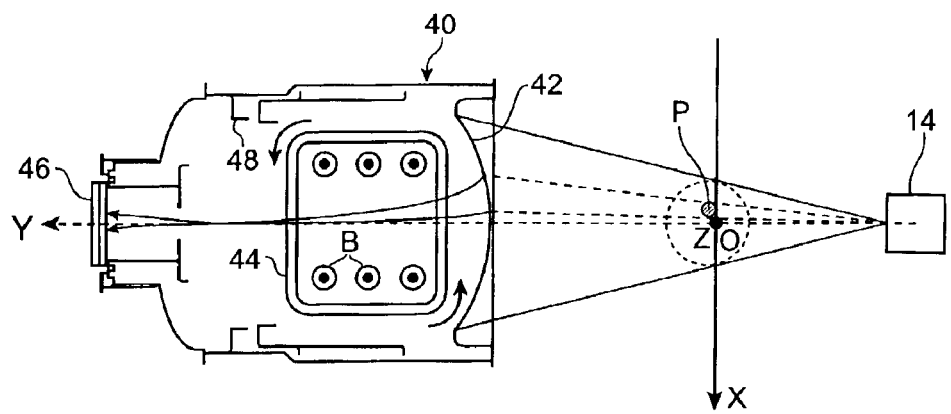
FIG. 3A, FIG. 3B and FIG. 3C are diagrams depicting the change of the electron orbit.
Figure 3B:
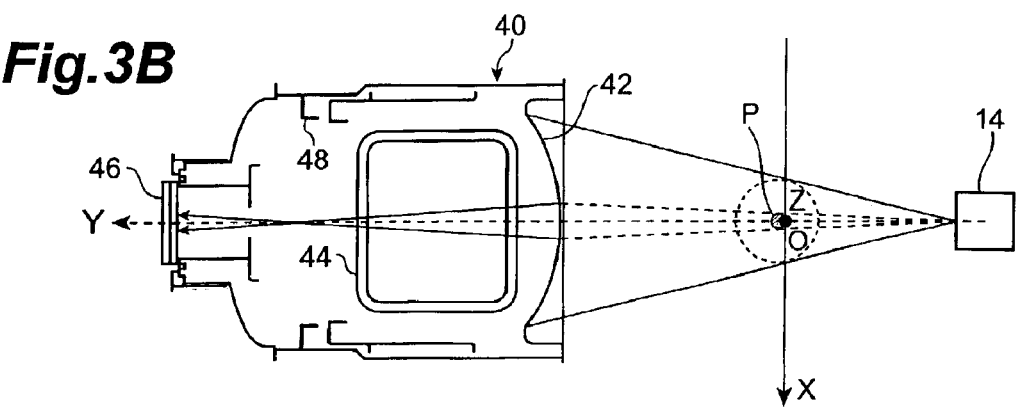
Figure 3C:
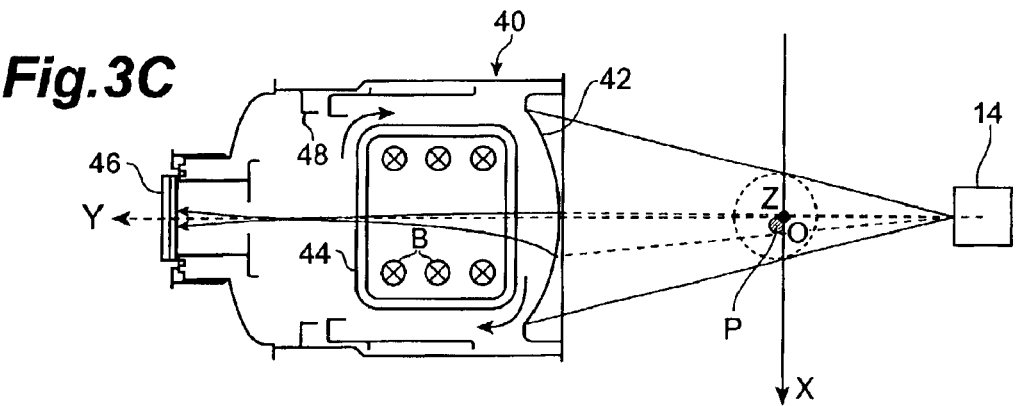

Now control of the deflection coil 44, which is a characteristic of the present embodiment, will be described with reference to FIG. 3A, FIG. 3B and FIG. 3C depicting the relationship of the deflection current to be conducted to the deflection coil 44 and the electron orbit. In FIG. 3A, FIG. 3B and FIG. 3C, the deflection coil 44 is shown inside the container 40 to clarify the conduction direction of the deflection current, where the moving direction of the tablet P is the X axis, the line connecting the pulse X-ray source 14 and the center of the X-ray electron conversion face 42 of the X-ray gate I•I 40 is the Y axis, and the axis from the back to the front of the page face is the Z axis, and the intersection of the X axis, Y axis and Z axis is the origin 0. FIG. 3A, FIG. 3B and FIG. 3C are diagrams depicting the states of the tablet P transported by the belt conveyor 12 passing the origin 0 in a time series.

As FIG. 3A shows, when the tablet P is in the negative area of the X axis (upper side of the Y axis in FIG. 3A), the X-ray image transmitted through the tablet P enters the negative area of the X axis on the X-ray electron conversion face 42. When the X-ray image enters the X-ray electron conversion face 42, an electronic image is emitted from the X-ray electron conversion face 42, and the emitted electronic image is accelerated by the accelerating electrode 48, and enters the output fluorescent face 46. In this process, as FIG. 3A shows, current flowing in the counterclockwise direction, shown in FIG. 3A, is conducted to the deflection coil 44, so as to generate the magnetic field B in the Z axis direction. By this, the electronic image flowing from the X-ray electron conversion face 42 to the output fluorescent face 46 shifts from the magnetic field B in the X axis direction by receiving Lorentz's force, and enters roughly the center of the output fluorescent face 46.

As FIG. 3B shows, when the tablet P moves and the tablet P comes to the origin 0, the transmitted X-ray image of the tablet P enters the center of the X-ray electron conversion face 42. In this case, it is unnecessary to generate the magnetic field B, and the electronic image emitted from the X-ray electron conversion face 42 enters the center of the output fluorescent face 46 as is.

As FIG. 3C shows, when the tablet P moves more and is in the positive area of the X axis (lower side of the Y axis in FIG. 3A), the transmitted X-ray image of the tablet P enters the positive area of the X axis on the X-ray electron conversion face 42. In this case, contrary to the case of FIG. 3A, current flowing in the clockwise direction, shown in FIG. 3C, is conducted through the deflection coil 44, and the magnetic field B in the negative direction of the Z axis is generated, so that the electronic image is deflected in the negative direction of the X axis, to enter the electronic image roughly at the center of the output fluorescent face 46.

Figure 4:
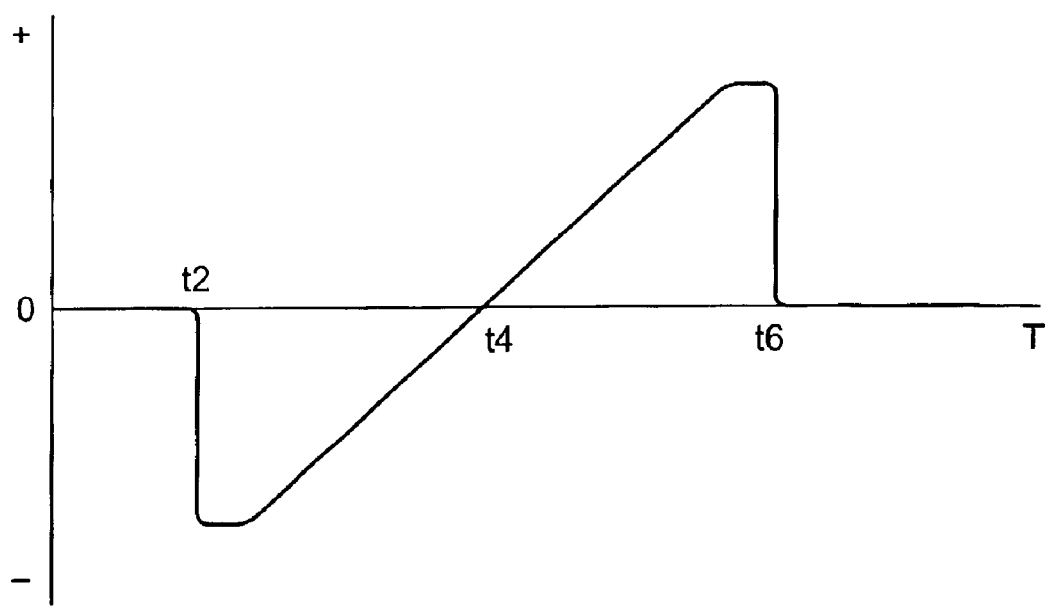
FIG. 4 is a diagram depicting the control of current to conduct through the deflection coil.

To generate the magnetic fields shown in FIG. 3A, FIG. 3B and FIG. 3C, the current to be conducted through the deflection coil 44 is as shown in FIG. 4, where the clockwise direction shown in FIG. 3A, FIG. 3B and FIG. 3C is "+". In other words, current in the "−" direction is conducted through the deflection coil 44 at time t2, and the amount of current is decreased as the tablet P approaches the origin 0. This is to decrease the amount of deflection as the tablet P approaches the origin 0. And at time t4 when the tablet P passes through the origin 0, the direction of the current is inverted, and is then controlled such that the amount of current is increased as the tablet P moves away from the origin 0. Then at time t6, the current is shut down to 0.

The current value to be conducted through the deflection coil 44 at this time is a value for deflecting the electronic image output from the X-ray electron conversion face 42, forming the X-ray fluoroscopic image at the center of the output fluorescent face 46. Therefore the amount of current to be conducted through the deflection coil 44 changes according to the position of the transmitted X-ray image, which enters the X-ray electron conversion face 42.

Since the pulse X-ray source 14 is a point light source, the position of the transmitted X-ray image to be projected onto the X-ray electron conversion face 42 is changed not only by the position of the tablet P in the X axis direction, but also by the position of the tablet P in the Y axis direction.

In the present embodiment, the position of the tablet P in the X axis direction is calculated by the elapsed time from the second light shielding time, but the position of the tablet P in the Y axis direction, that is, the distance from the pulse X-ray source 14, can also be detected since the first light blocking time is also acquired, and as a result, the position and the moving speed of the X-ray image, which transmits through the tablet P and enters the X-ray electron conversion face 42, can be calculated. This aspect will now be described with reference to FIG. 5. As FIG. 5 shows, the positional relationship of each element constituting the measurement object detecting means 30 is that the first photo-diode 34 and the second photo-diode 36 are disposed in parallel with the moving direction of the tablet P separated from each other at distance d, and the distance between the line connecting each light receiving face of the two photo-diodes 34 and 36 and the light emitting diode 32 is D.

If the interval between the first light blocking time and the second light blocking time in this state is Δt, then the moving distance of the table P during this time is VΔt. Using the similar relationship of the triangles, the space between the locus of the tablet P and the light emitting diode 32 is calculated as $$X = D \times V\Delta t/d \quad (1)$$

Figure 5:
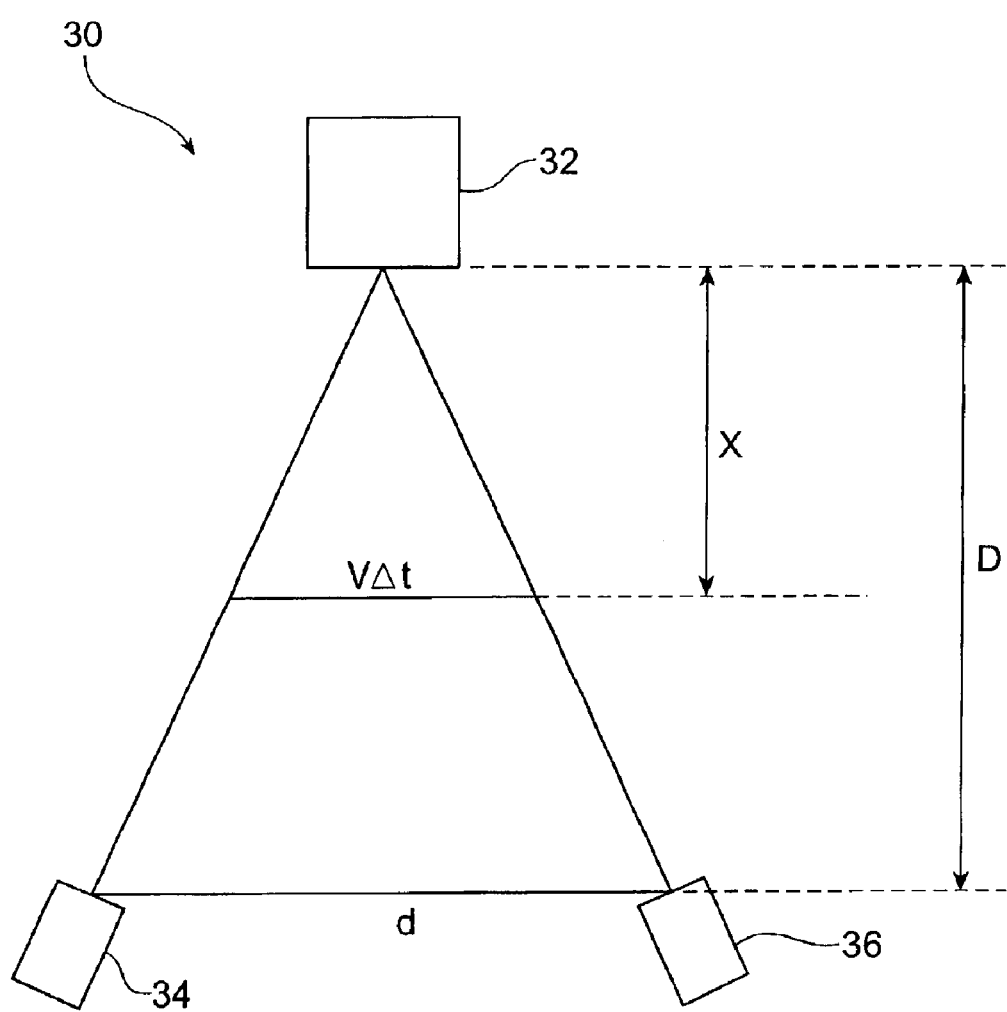
FIG. 5 is a diagram depicting the method of calculating position by the position detecting means.

If the pulse X-ray source 14 and the X-ray gate I•I 40 are disposed at the positions corresponding to the light emitting diode 32 and the photo-diodes 34 and 36 shown in FIG. 5, then the moving speed V' of the transmitted X-ray image which enters the X-ray electron conversion face 42 is $$V' = V \times D/X \quad (2)$$

and substituting (1) for (2)

$$V' = d/\Delta t$$

is calculated. Based on this result and on the elapsed time from the second light blocking time, the position of the X-ray image, which transmits through the tablet P and enters the X-ray electron conversion face 42, can also be calculated, so the amount of current to be conducted through the deflection coil 44 can be controlled.

In this way, by controlling the current to be conducted through the deflection coil 44 and generating the magnetic field B for deflecting the electron orbit, the X-ray fluoroscopic image to be projected onto the output fluorescent face 46 always enters at the center of the output fluorescent face 46 when the tablet P passes through the origin 0, and during this time, the X-ray fluoroscopic image of the tablet P looks as if it is standing still at the center of the output fluorescent face 46.

Figure 6:
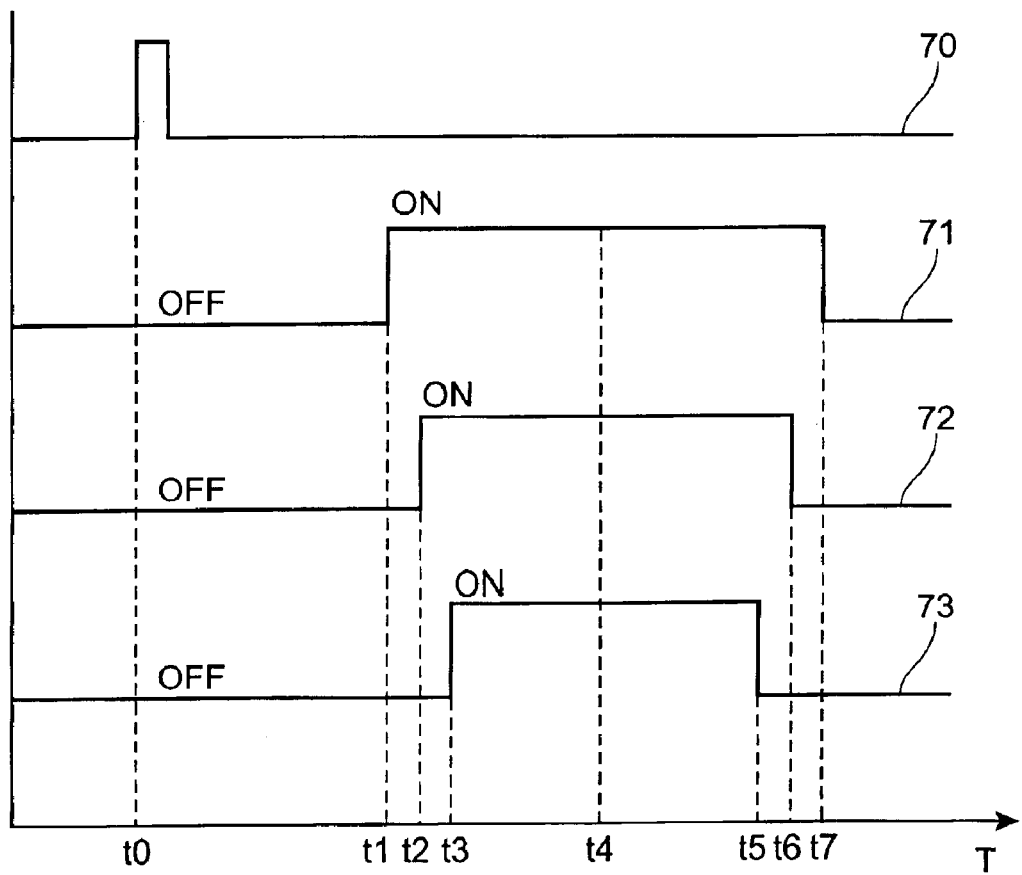
FIG. 6 is a timing chart depicting control by the timing circuit.

Now the timing signals, which are output from the timing circuit 20 to the X-ray power supply 22, deflection circuit 24, and X-ray gate power supply 26, will be described. The X-ray power supply 22, deflection circuit 24 and X-ray gate power supply 26 are all controlled based on the elapsed time from the second light blocking time t0. FIG. 6 is a chart depicting the respective timing.

As FIG. 6 shows, at time t0, the tablet P is detected by the second photo-diode 36, and the signal 70 from the second photo-diode 36 to the timing circuit 20 turns ON. The timing circuit 20 calculates time t3 when the tablet P enters the image capturing range, and calculates time t5 when the tablet P leaves the image capturing range, since the transporting speed V of the belt conveyor 12 is constant, and the timing circuit 20 turns the timing signal 73 to the X-ray gate power supply 26 ON when the tablet P is within the image capturing range, that is, applies voltage such that the output fluorescent face 46 side becomes high potential by the accelerating electrode 48, and captures the X-ray fluorescence image of the tablet P. And the timing circuit 20 turns the timing signal 71 from the timing circuit 20 to the X-ray power supply 22 ON at time t1, which is before time t3, to output an X-ray from the pulse X-ray source 14, and turns the timing signal 72 from the timing circuit 20 to the deflection circuit 24 ON at time t2, which is somewhere between time t1 and time t3, to conduct the current to the deflection coil 44.

Figure 7:
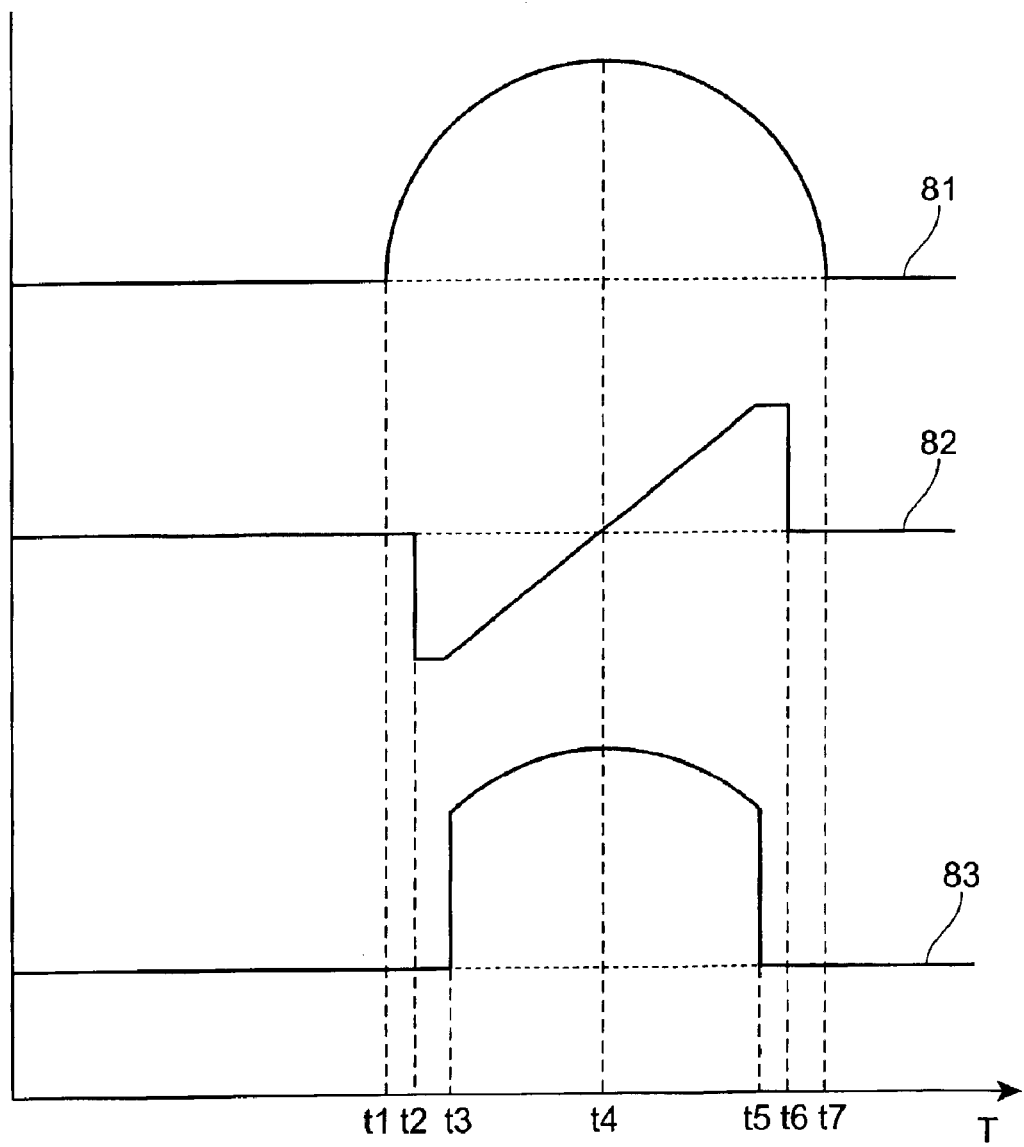
FIG. 7 is a diagram depicting signals at the pulse X-ray source, deflection circuit and X-ray gate I•I.

FIG. 7 shows the change of X-ray intensity which is output from the pulse X-ray source 14 at this time, and the change of current which flows through the deflection coil 44. The X-ray intensity 81, after being output from the pulse X-ray source 14 at time t1, rises rapidly and roughly stabilizes at around the maximum intensity of the X-ray, and then decreases toward time t7 when the output of the X-ray is stopped. The amount of current 82 which flows through the deflection coil 44 deflects at around time t2, when current begins to flow and at time t7 when the current is stopped, but basically changes occur linearly with respect to the time axis from time t2 to time t6.

Since the X-ray which is output from the pulse X-ray source 14 does not have a perfect pulse form, but has rise and fall portions and current which flows through the deflection coil 44 is deflected at the start and end of X-ray output, so an accurate image cannot be captured during these times.

In the X-ray inspection system of the present embodiment, the X-ray gate I•I 40 is used, and the gate of the X-ray gate I•I 40 is opened to capture the X-ray fluorescopic image of the tablet P when the current, which flows through the pulse X-ray power supply 14 and deflection coil 44, is stable, that is, during the time from time t3 to t5. By this, as FIG. 7 shows, the dose of X-ray 83, which enters through the X-ray gate I•I 40, can have roughly a pulse form. For the deflection current 82 as well, deflection distortion, which is generated at the start and end of deflection, can be avoided.

The X-ray fluoroscopic image acquired by the X-ray gate I•I 40 is captured by the CCD camera 18, and is sent to the processing judgment device 28. The processing judgment device 28 performs such processing as selecting the tablet P based on the captured X-ray fluoroscopic image.

In the X-ray inspection system 10 of the present embodiment, the deflection coil 44 is installed in the X-ray gate I•I 40, the orbit of the electronic image which is emitted from the X-ray electron conversion face 42 is deflected, so as to form an image roughly at the center of the output fluorescent face 46, without depending on the position of the tablet P. As a result, the image of the moving tablet P can be stood still on the output fluorescent face 46 and captured, so an exposure time can be secured and sensitivity can be increased even if the moving speed of the tablet P is increased.

Figure 8:
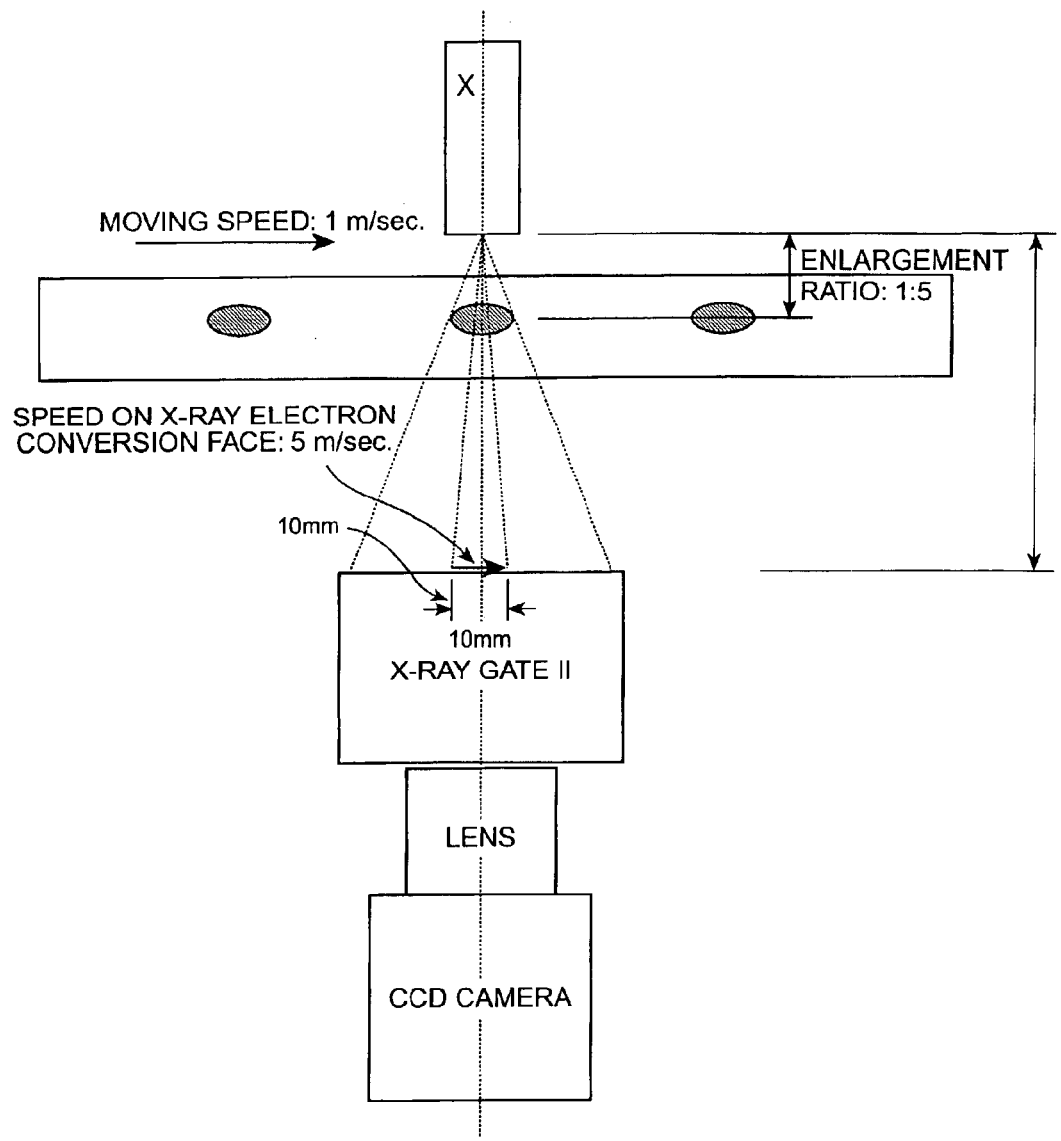
FIG. 8 is a diagram depicting the relationship between the deflection distance and exposure time.

This aspect will now be described based on the concrete example shown in FIG. 8. In the X-ray inspection system 10 shown in FIG. 8, the tablet P, placed on the belt conveyor 12, is moving to the right in FIG. 8 at speed 1 (m/s). The tablet P moves on the line which divides the line between the pulse X-ray source 14 and the X-ray gate I•I 40 internally at 1:5, so the transmitted X-ray image of the tablet P, which enters the X-ray electron conversion face 42 of the X-ray gate I•I 40, moves to the right in FIG. 8 at speed 5 (m/s).

In order to capture an image of the tablet P at resolution 0.5 (mm) in this case, the X-ray gate must be controlled so that the shutter time T becomes T=0.5 (mm)/(5000 (mm/s))=1/10000 (s). However, capturing an image at a shutter time of 1 (ms) or less is actually impossible, since sensitivity is insufficient.

The X-ray inspection system 10 of the present embodiment can deflect the orbit of the electron which is output from the X-ray electron conversion face 42 while the transmitted X-ray image moves for 10 (mm), for example, on the X-ray electron conversion face 42, so as to make the X-ray image stand still on the output fluorescent face 46. By this, 10 (mm)/0.5 (mm)=20 (times), that is, a 2 (ms) sufficient exposure time can be obtained.

As the above concrete example shows, the X-ray inspection system 10 of the present embodiment can secure both the required resolution and sensitivity when the tablet P moving at a high speed is observed.

Figure 9:
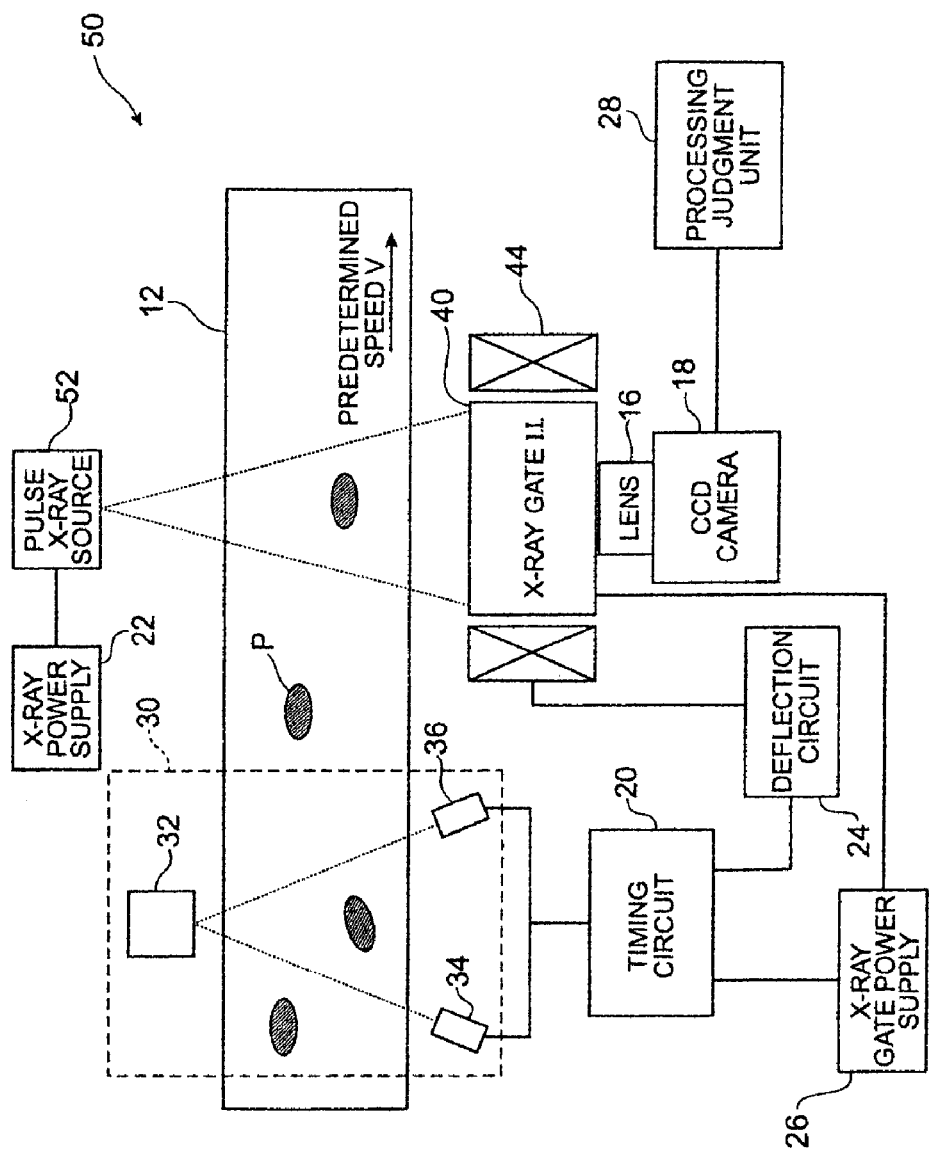
FIG. 9 is a block diagram depicting an X-ray inspection system according to the second embodiment.

Now the second embodiment of the present invention will be described. The X-ray inspection system 50 of the second embodiment shown in FIG. 9 has basically the same configuration as the X-ray inspection system 10 of the first embodiment, but the difference is that the X-ray source 52 is used instead of the pulse X-ray source 14.

Figure 10:
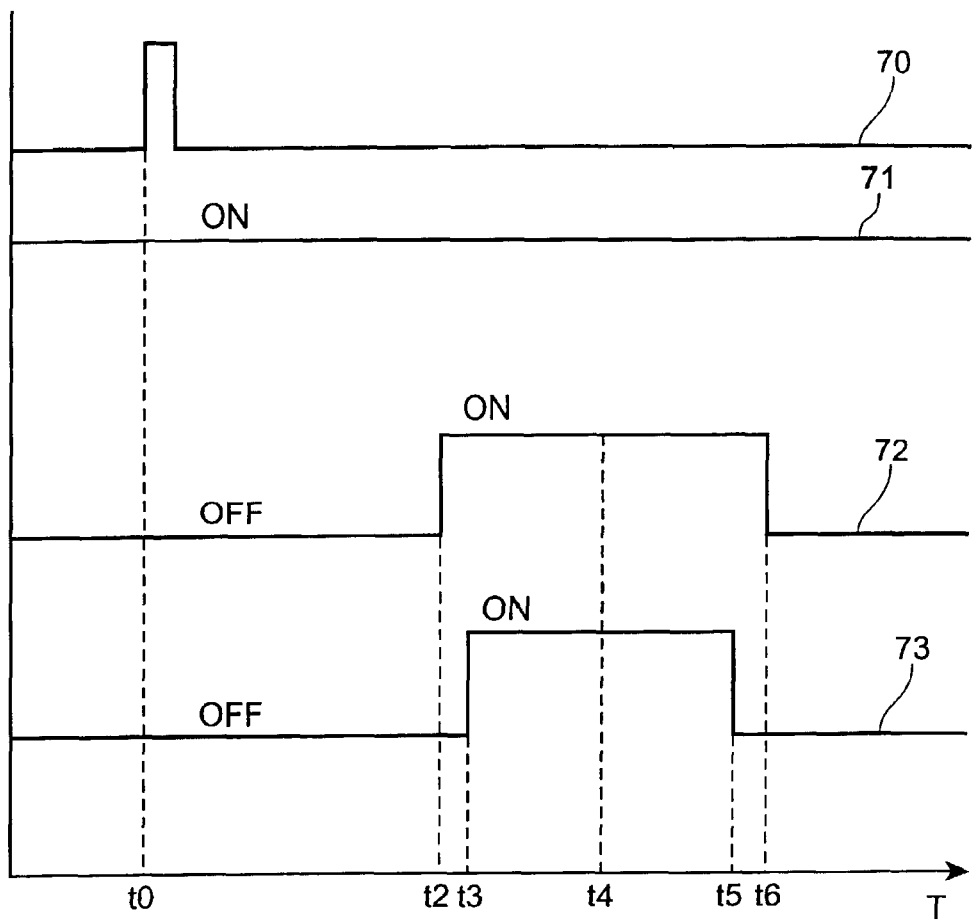
FIG. 10 is a timing chart depicting control by the timing circuit.
Figure 11:
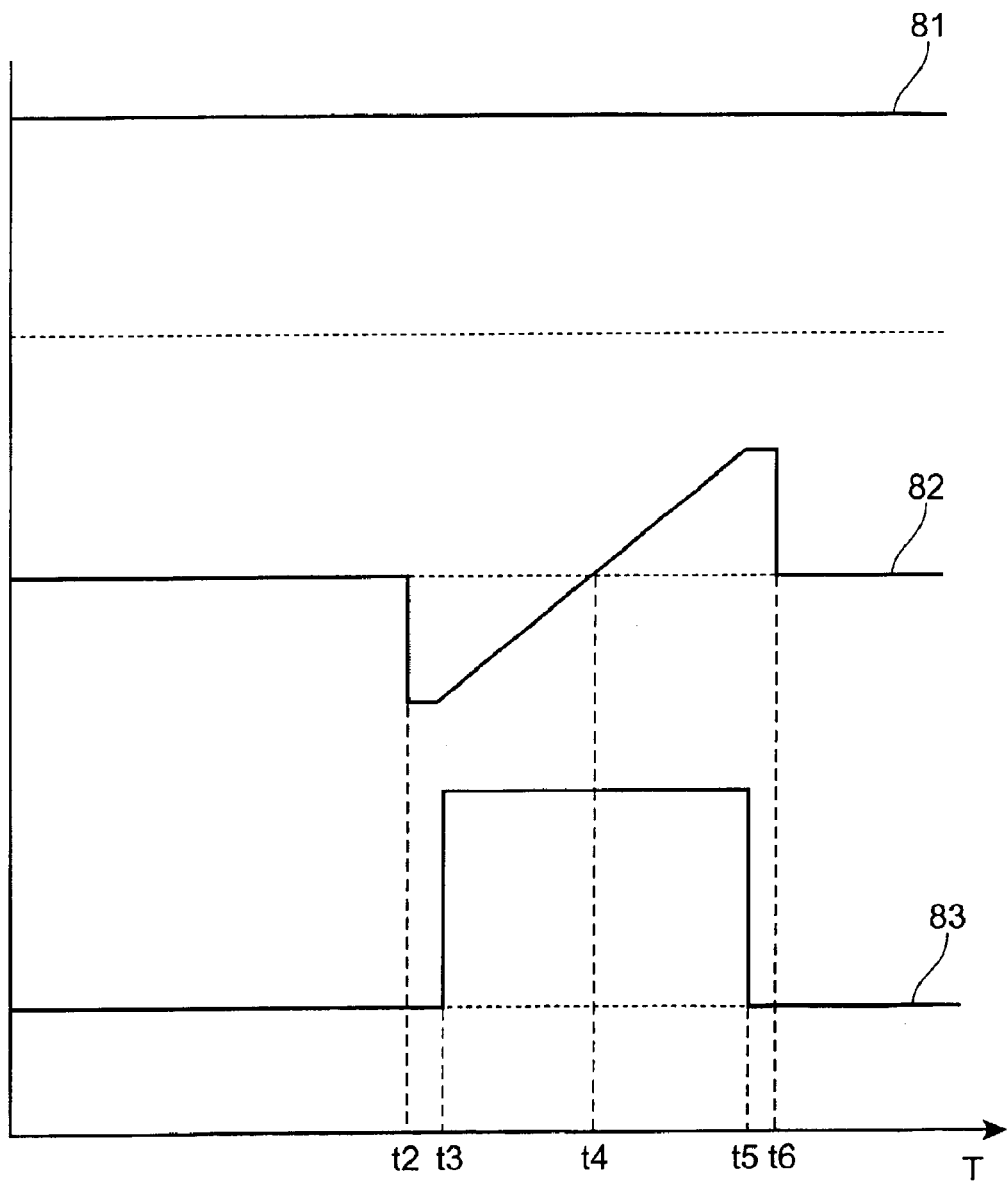
FIG. 11 is a diagram depicting signals at the pulse X-ray source, deflection circuit and X-ray gate.

In the second embodiment, the X-ray source 52 is continuously ON, and the timing circuit 20 does not control the X-ray power supply 22, as shown in FIG. 10. In other words, the ON signal 71 is constantly input from the power supply circuit, which is not illustrated, to the X-ray power supply 22. The timing circuit 20 turns the timing signal 73 to the deflection circuit 24 ON at time t2, then turns the timing signal 74 to the X-ray gate power supply 26 ON at time t3, to capture images. This makes control by the timing circuit 20 easier, and a complete pulse X-ray viewed from the X-ray gate I•I 40 can be obtained, as shown in FIG. 11, since an X-ray is output continuously.

Figure 12:
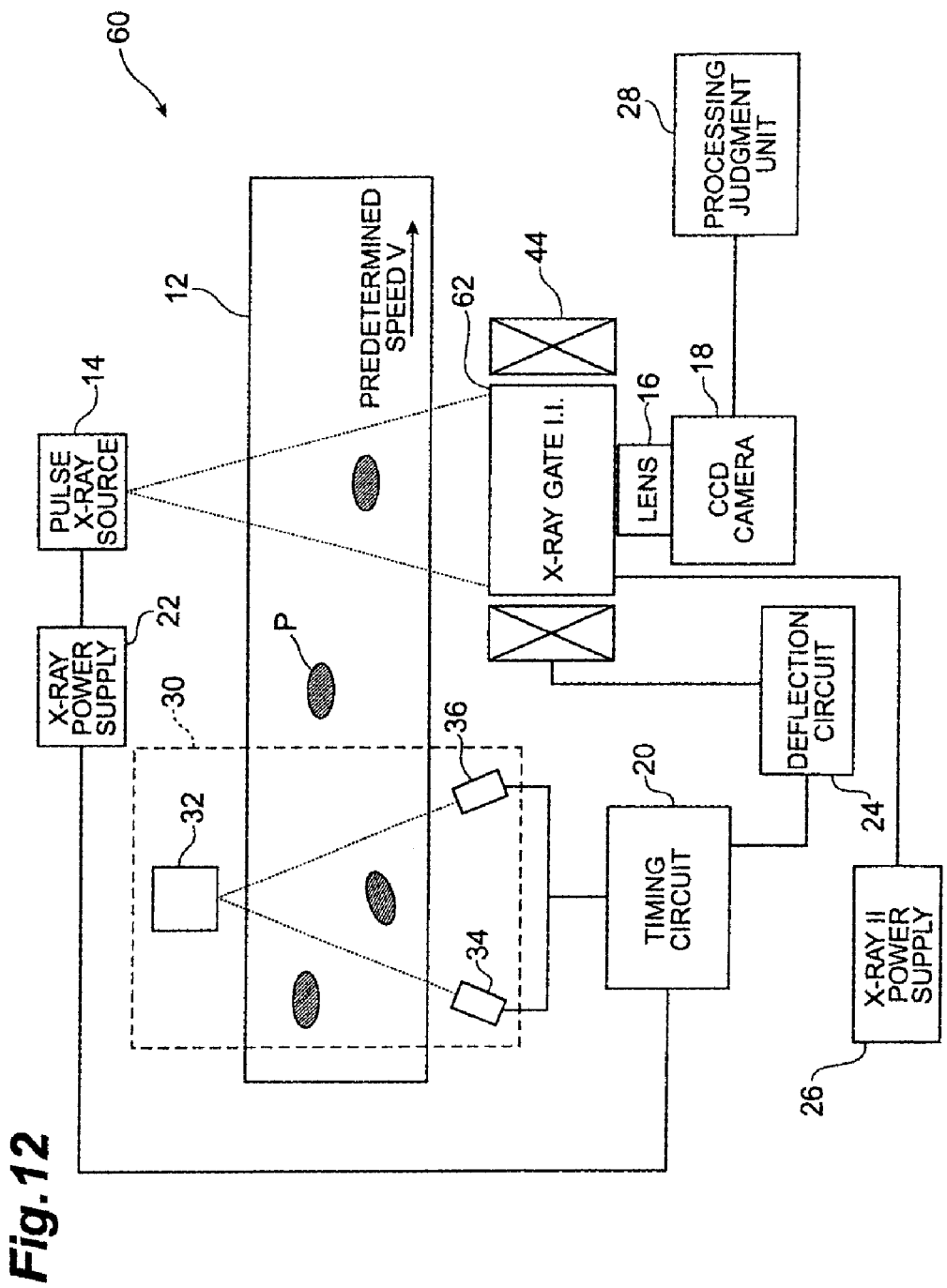
FIG. 12 is a block diagram depicting an X-ray inspection system according to the third embodiment.

Now the third embodiment of the present invention will be described. The X-ray inspection system 60 of the third embodiment shown in FIG. 12 has basically the same configuration as the X-ray inspection system 10 of the first embodiment, but the difference is that the X-ray II 62, which does not have a gate function, is used instead of the X-ray gate I•I 40.

Figure 13:
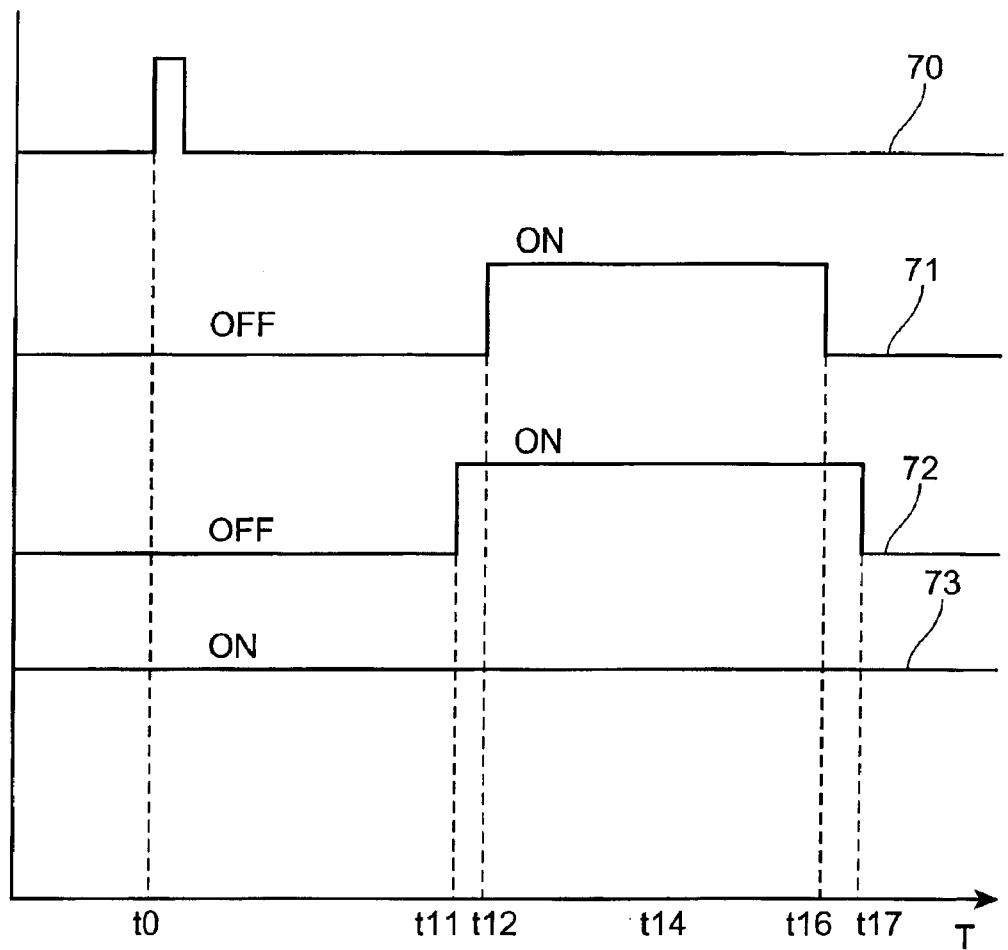
FIG. 13 is a timing chart depicting control by the timing circuit.
Figure 14:
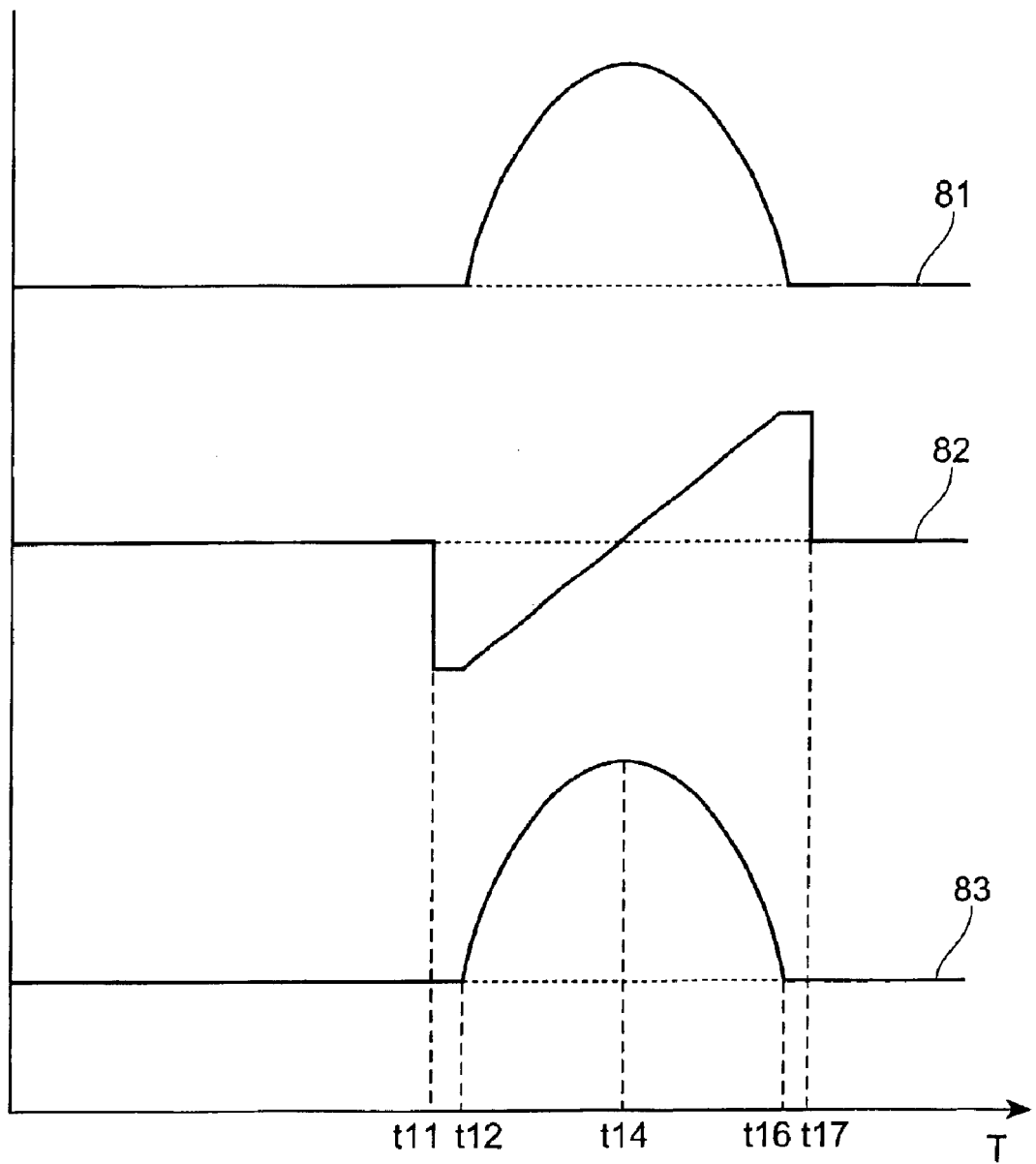
FIG. 14 is a diagram depicting the pulse X-ray source, deflection circuit and X-ray gate.

In the third embodiment, the X-ray II 62 is continuously ON, and the timing circuit 20 does not control the X-ray gate, as shown in FIG. 13. In other words, the ON signal 73 is constantly input from the power supply circuit, which is not illustrated, to the X-ray gate power supply 26. And the timing circuit 20 turns the timing signal 72 to the deflection circuit 24 ON at time t11, and then turns the timing signal 71 to the X-ray power supply 22 ON at time t12. This makes control by the timing circuit 20 easier, and distortion of the deflection current 82 can be avoided, as shown in FIG. 14.

The embodiments of the present invention have been described in detail, but the present invention is not limited to the above embodiments.

In the above embodiments, a combination of one light emitting diode 32 and two photo-diodes 34 and 36 is used as the measurement object detecting means 30 of the tablet P, and the position of the tablet P is calculated by this measurement object detecting means 30 and elapsed time, but the detection of the position of the tablet P is not limited to these embodiments. For example, an image of the tablet P is captured using a video camera, and the position of the tablet P, which passes through the image capturing range, may be analyzed.

When the moving path of the tablet P is limited to a narrow range, or when the moving path of the tablet P is close to the X-ray gate I•I side and the moving speed of the transmitted X-ray image projected on the X-ray gate I•I does not change much depending on the change of the moving path of the tablet P, the measurement object detecting means may be a combination of one light emitting diode and one photo-diode.

The above mentioned X-ray inspection system is an X-ray inspection system comprised of an X-ray source 14 and an X-ray image capturing unit 40 (16, 18), which are installed facing each other, sandwiching the passing path of the measurement object P, wherein the X-ray image capturing unit 40 has the X-ray electron conversion material 42 and the output fluorescent face 46 facing the X-ray electron conversion material 42, and the X-ray image capturing unit 40 deflects the flow of an electronic image between the X-ray electron conversion material 40 and the output fluorescent face 46 at a speed synchronizing with the moving speed of the measurement object P.

Since the flow of an electronic image between the X-ray electron conversion material 40 and the output fluorescent face 46 is deflected at a speed synchronizing with the moving speed of the measurement object P, the image capturing time of the measurement object P can be increased, and therefore both the required resolution and sufficient sensitivity can be implemented.

The above mentioned X-ray inspection system starts deflection according to a predetermined trigger which is generated based on the position of the measurement object P. Since time when the measurement object P arrives in the space between the X-ray source 14 and the X-ray image capturing unit 40 can be determined, the deflection is started synchronizing with this arrival time, and the flow of an electronic image is deflected synchronizing with the moving speed of the measurement object P. In other words, the output of the timing circuit 20 is a predetermined trigger which is generated based on the position of the measurement object P, and the above mentioned deflection is started according to this trigger.

In the above mentioned X-ray inspection system, the position of the measurement object P is detected without contact, and the above mentioned trigger is generated based on the detected position.

This configuration may be such that the position of the measurement object P is detected using physical contact, and the above mentioned trigger is generated based on the detected position.

Figure 15:
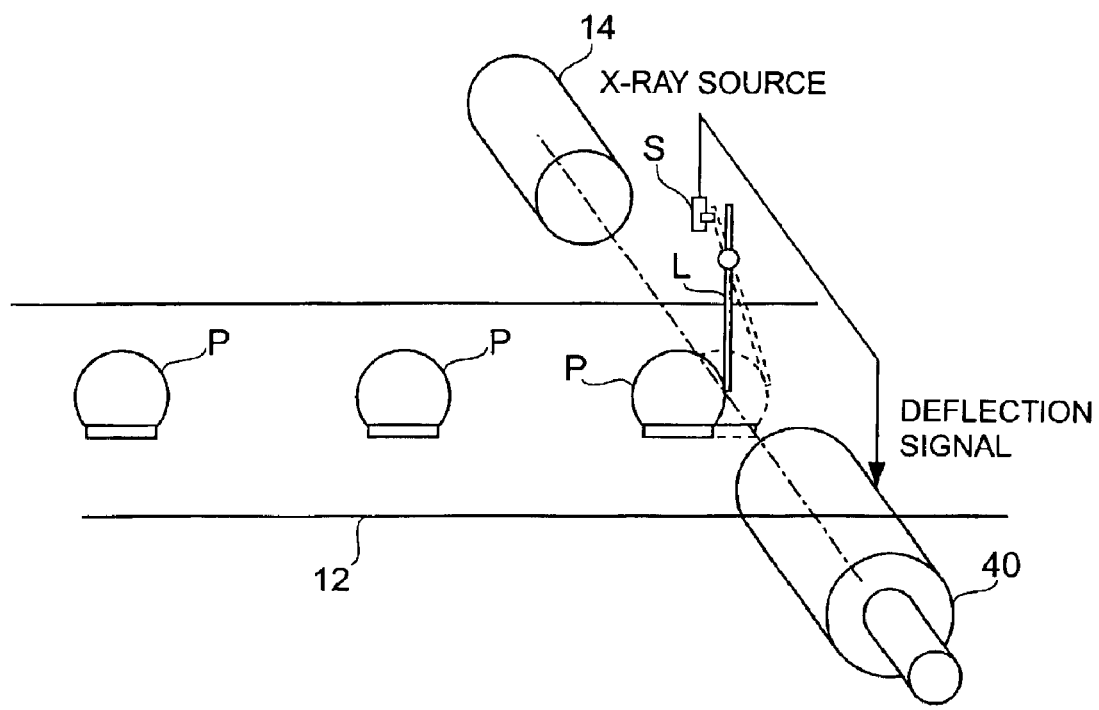
FIG. 15 is a diagram depicting the X-ray inspection system.

FIG. 15 is a diagram depicting the X-ray inspection system with such a configuration, and only the aspects which are different from the above mentioned embodiment are shown. When the measurement object P reaches a specified position on the belt conveyor 12, the lever L is pressed by the measurement object P, and the switch S installed on the moving path of the lever L is turned ON, and the trigger (deflection signal) is output synchronizing with this.

The above mentioned X-ray inspection system may comprise restricting means for restricting the position of the measurement object, and releasing means for releasing the restriction, wherein the above mentioned trigger is generated when a predetermined time has elapsed after the above mentioned release operation.

Figure 16:
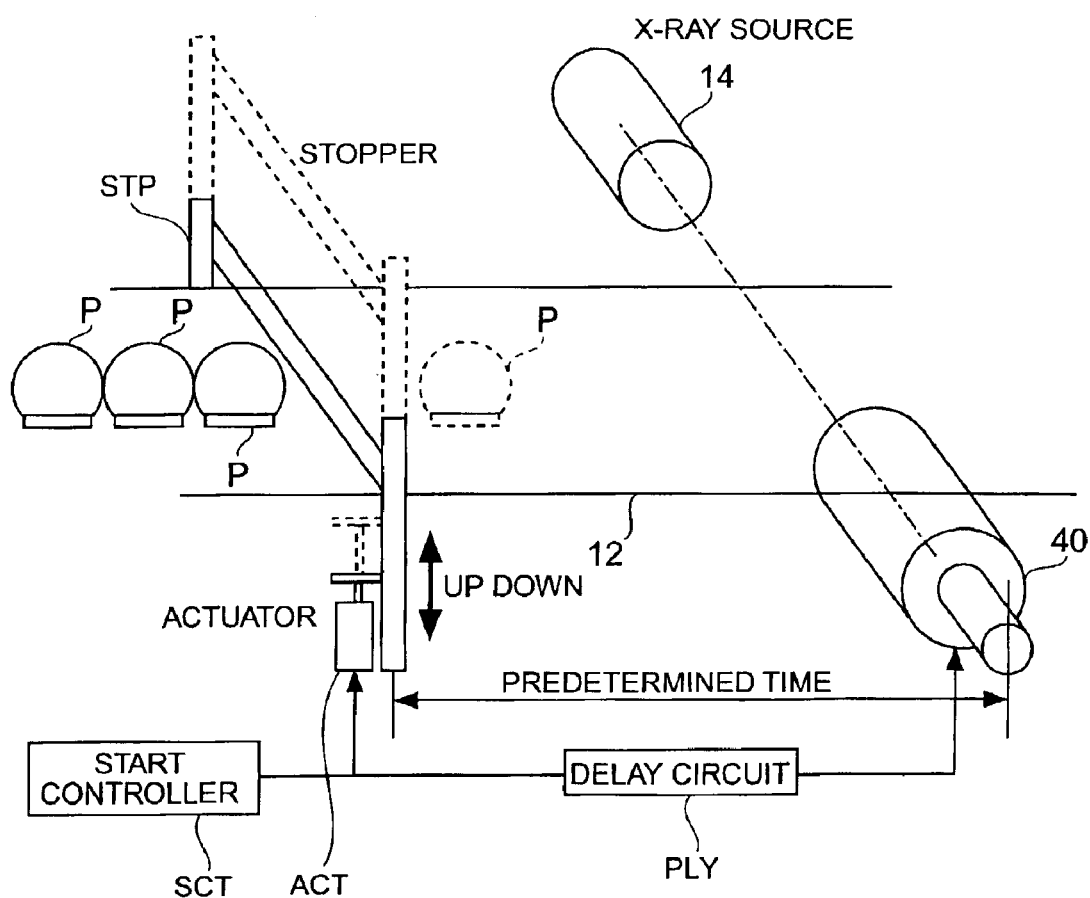
FIG. 16 is a diagram depicting the X-ray inspection system.

FIG. 16 is a diagram depicting the X-ray inspection system with such a configuration, and only the aspects which are different from the above mentioned embodiment are shown. When the measurement object P is restricted at a specified position on the belt conveyor 12 by the restricting means (stopper STP and actuator ACT secured to the stopper STP), and when the actuator ACT moves up, the stopper is released and functions as the releasing means. This releasing operation is executed by the trigger provided from the start controller SCT to the actuator ACT, but the trigger is provided to the X-ray gate I•I 40 as the deflection signal via the delay circuit DLY. Therefore the trigger to start deflection is generated when a predetermined time has elapsed from the above mentioned release operation. The predetermined time is pre-calculated based on the moving speed of the belt conveyor 12 and the distance up to the image capturing position.

In the above mentioned X-ray inspection system, deflection maybe performed independently from the position of the measurement object P.

Figure 17:
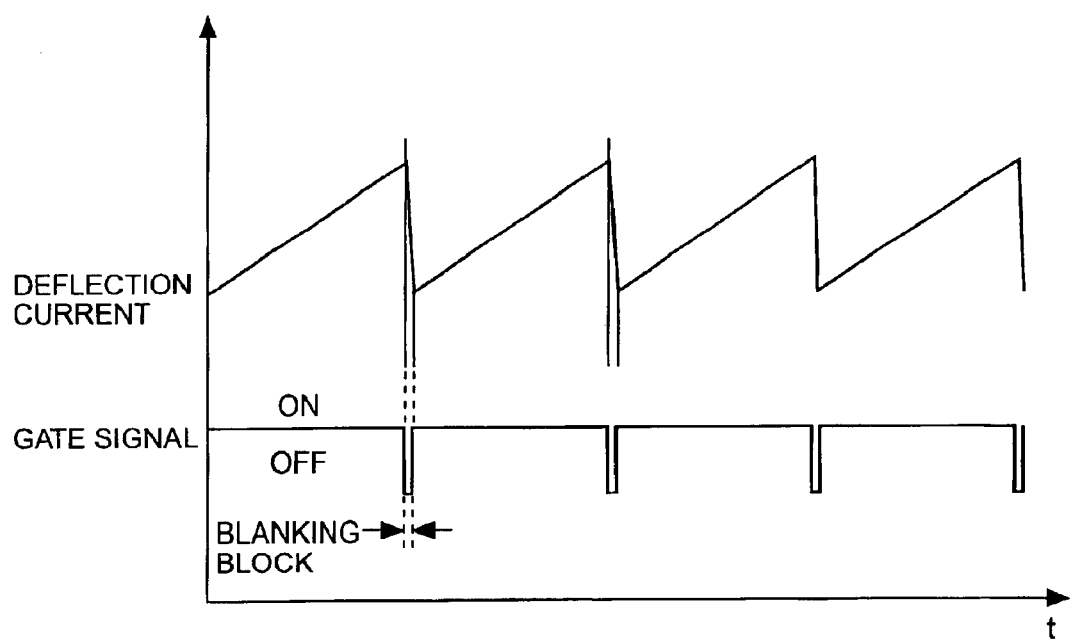
FIG. 17 is a timing chart depicting the deflection current to be supplied to the X-ray inspection system X-ray gate I•I 40 and gate signals.

FIG. 17 is a timing chart of the deflection current and gate signal to be provided to the deflection coil 44 of the X-ray gate I•I 40 of the X-ray inspection system with such a configuration. The difference from the X-ray inspection system shown in FIG. 1 is that deflection is performed independently from the position of the measurement object P. By flowing the deflection current, which matches the speed of the belt conveyor 12 (specifically, the speed of the X-ray image on the photo-electric face of the X-ray gate II of the measurement object P) into the deflection coil 44 as the deflection signal, a still image can be constantly captured. The deflection current has a saw tooth wave. And the gate signal of the X-ray gate I•I 40 is turned OFF in the blanking section of the saw tooth wave. When the gate signal is OFF, the output of the X-ray image capturing unit is inhibited. Therefore an even clearer image can be obtained. For capturing an output image, either the measurement object P is moved by an interval (1/30 sec.) matching the NTSC system (1 frame per 1/30 sec.), or a high speed camera, for which the image capturing time can be freely set, is used.

In the X-ray inspection systems shown in FIG. 1 and FIG. 2, the X-ray image capturing unit has a CCD camera 18 which is installed facing the output fluorescent face 46, but the position of the measurement object P may be detected by its own image capturing mechanism, that is, the CCD camera 18. When the measurement object P is detected at the edge of the image output from the CCD camera 18, the image signal constituting this image changes, so this signal change is detected and deflection is started. The time when the measurement object reaches the position to be image-captured at the center of the X-ray gate I•I 40, and the deflection speed synchronizing with the moving can be calculated based on the moving speed of the belt conveyor 12.

Also in the above mentioned X-ray inspection system, the above mentioned trigger may be generated by the operator, who visually observes the measurement object P and turns the switch ON (an equivalent corresponds to the timing circuit 20 in FIG. 1) for starting deflection.

In the above mentioned X-ray inspection system, the belt conveyor 12 moves at a constant speed, but this speed may not be constant. In other words, if the speed of the belt conveyor 12 is detected in real-time by an encoder, the above mentioned deflection may be performed according to the moving speed of the measurement object P.

According to the above mentioned X-ray inspection system, the image of the moving measurement object can be captured at high sensitivity and high resolution by using the X-ray image capturing unit having a deflection function.

Industrial Applicability

The present invention can be applied, to an X-ray inspection system which inspects a measurement object based on the X-ray fluoroscopic image of the measurement object moving at a predetermined speed, particularly to an in-line non-destructive inspection device for inspecting a measurement object to be transported by a belt conveyor.

What is claimed is:

1. An X-ray inspection system comprising:
  an X-ray source for irradiating an X-ray onto a moving measurement object;
  an X-ray image capturing unit which has an X-ray electron conversion face for converting an entered X-ray image corresponding to said measurement object into an electronic image and an output face where said electronic image emitted from said X-ray electron conversion face enters, and an X-ray fluoroscopic image of said measurement object corresponding to said entered electronic image is output;
  position detecting means for detecting the position of said measurement object; and
  deflecting means for deflecting the flow of said electronic image from said X-ray electron conversion face to said output face and forming said electronic image on a predetermined area of said output face based on the position of said measurement object detected by said position detecting means.

2. The X-ray inspection system according to claim 1, wherein said X-ray source is a pulse X-ray source which outputs the X-ray when said measurement object is within the image capturing range of said X-ray image capturing unit.

3. The X-ray inspection system according to claim 2, characterized in that:
  said X-ray image capturing unit further comprises an electrode which controls the flow of said electronic image to said output face by applying a voltage between said X-ray electron conversion face and said output face; and
  said electrode cancels control of the flow of said electronic image after the X-ray is output from said pulse X-ray source, and controls the flow of said electronic image before the output of the X-ray from said pulse X-ray source is stopped.

4. The X-ray inspection system according to claim 1, wherein said X-ray image capturing unit further comprises an electrode which controls the flow of said electronic image to said output face by applying a voltage between said X-ray electron conversion face and said output face.

5. The X-ray inspection system according to claim 1, wherein said X-ray source is a point light source.

6. The X-ray inspection system according to claim 1, wherein said output face is a fluorescent face which emits fluorescence by the entry of said electronic image.

7. The X-ray inspection system according to claim 1, characterized in that:
  said position detecting means further comprises measurement object detecting means for detecting said measurement object before reaching the image capturing range of said X-ray capturing unit; and
  the position of said measurement object in the image capturing range is determined based on the detection of said measurement object by said measurement object detecting means and the elapsed time from the time when said measurement object is detected.

8. The X-ray inspection system according to claim 7, characterized in that:
  said measurement object detecting means further comprises one light emitting element which emits light onto said measurement object, and two light receiving elements which are installed at different locations and receive light output from said light emitting element; and
  the distance of the moving path of said measurement object and said light emitting element are detected from the time interval of the time when the light output from said light emitting element to each one of said light receiving elements is blocked by said measurement object.

* * * * *